United States Patent [19]
Bonnet

[11] Patent Number: 5,622,428
[45] Date of Patent: Apr. 22, 1997

[54] METHOD AND APPARATUS FOR DETERMINATION OF A CRITERION OF ACTIVITY OF A RATE MODULATION PARAMETER SENSOR IN AN ACTIVE IMPLANTABLE MEDICAL DEVICE

[75] Inventor: Jean-Luc Bonnet, Vanves, France

[73] Assignee: Ela Medical S.A., Montrouge, France

[21] Appl. No.: 578,967

[22] Filed: Dec. 27, 1995

[30] Foreign Application Priority Data

Dec. 30, 1994 [FR] France ................................. 94 15912

[51] Int. Cl.$^6$ .................................................. G06F 15/00
[52] U.S. Cl. ........................................... 128/630; 128/920
[58] Field of Search ......................... 607/17; 364/413.01

[56] References Cited

FOREIGN PATENT DOCUMENTS

| | | | |
|---|---|---|---|
| 0317065A2 | 10/1988 | European Pat. Off. | A61N 1/365 |
| 0746595 | 7/1980 | U.S.S.R. | 364/413.01 |
| WO9308873 | 5/1993 | WIPO | A61N 1/36 |
| WOA9320889 | 10/1993 | WIPO | A61N 1/365 |

*Primary Examiner*—William E. Kamm
*Attorney, Agent, or Firm*—Orrick, Herrington & Sutcliffe LLP

[57] ABSTRACT

The process of determining a criterion of activity of a sensor used to measure a parameter of enslavement in an active implantable medical device. The process is characterized by the following steps:

a) acquisition of successive samples of the representative value of the parameter from a signal collected by the sensor, b) calculation over a first interval of time of a first average value (AVE_SENSOR_SHORT_TERM) of the activity from the samples acquired by the sensor;

c) calculation over a second interval of time, greater than the first, of a second average value (AVE_SENSOR_24H) of the activity of the sensor from acquired samples, and d) determination of a criterion of activity of the sensor, by comparison of the first average value and the second average value, notably by giving to the criterion of activity a first value (Rest) defining a state of rest of the patient if the first average value (AVE_SENSOR_SHORT_TERM) is less than the second average value (AVE_SENSOR_24H), and a second value (Non-Rest) defining a state of non-rest of the patient in the opposite case.

27 Claims, 8 Drawing Sheets

METHOD AND APPARATUS FOR DETERMINATION OF A CRITERION OF ACTIVITY OF A RATE MODULATION PARAMETER SENSOR IN AN ACTIVE IMPLANTABLE MEDICAL DEVICE

FIELD OF THE INVENTION

The present invention concerns "active implantable medical devices", such those defined by the European Community Council Directive 90/385/CEE, of 20 Jun. 1990, and in particular to cardiac pacemakers or defibrillators, whose functioning is enslaved to a sensed parameter using a sensor to measure the parameter. To this end, although the following description mainly refers to the case of an enslaved cardiac pacemaker, the invention is easily applicable to a wide variety of electronic devices other than active implantable medical devices.

BACKGROUND OF THE INVENTION

Enslaved devices are known to adapt their actions, for example, the stimulation frequency in the case of a cardiac pacemaker, to the measured value or a value calculated value from a representative parameter of metabolic needs of the wearer of the device. In this regard, the term "enslaved" should be generally understood to mean a device having a mode of operation that senses a parameter and operates according to a function that relates the sensed parameter to a desired operating condition. Most typically, one refers to a pacemaker that is enslaved to a physiological parameter, meaning that it has a sensor that senses a physiological parameter indicative of the patient's cardiac output requirements, and then implements a pacing rate that is determined as a function of that parameter. Such pacemakers are also referred to as rate responsive or rate modulated pacemakers, because the pacing rate varies (or is modulated) according to the sensed needs of the patient.

EP-A-0 089 014 describes the utilization of the measure of the respiratory frequency (breathing rate) to vary the instantaneous cardiac stimulation frequency. Several other parameters, such as the minute ventilation (also known as minute volume), the saturation of oxygen in the blood, the blood or body temperature and the acceleration (e.g., physical motion) have been used as enslavement (rate modulation or rate responsive) parameters.

In the case of cardiac pacemakers, all these systems operate to increase the frequency of stimulation pulses when one detects an increasing activity of the patient wearing the device (i.e., the patient in which the device is implanted or on which the device is carried), and to decrease this frequency to a base value in the case of a diminution of activity, particularly during phases of rest of the patient.

EP-A-0 493 222 describes a process of correlation between, on the one hand, the two extreme values $Fc_{base}$ and $Fc_{max}$ of the range of the stimulation frequency and, on the other hand, value $X_{base}$ and $X_{max}$, which are respectively the rest value and the value of maximal activity, calculated from information collected by the enslavement sensor. This process of correlation is known under the name of "automatic calibration of the enslavement", and the document describes a process to determine the value of $X_{base}$ in the case of the utilization of the minute—ventilation as the parameter of enslavement. The value of the minute—ventilation at rest is then called "$VE_{REPOS}$". This last value is obtained by the calculation of an average value during an interval on the order of 24 hours, including, therefore, periods of activity as well as periods of sleep of the wearer of the device.

The inventors have nevertheless observed and recognized that, during phases of sleep, the values of $VE_{REPOS}$ can be more than 50% below the values of this same parameter recorded during periods when the patient is awake (i.e., conscious) and active.

In the aforementioned document, such important variations are not and cannot be taken into consideration. Nevertheless, this value of $VE_{REPOS}$ is used for the automatic calibration of the enslavement of the device during the adjustment of the operating point relative to the minimal stimulation frequency $FC_{base}$.

THUS, as the inventors have realized, a false or incorrect estimation of the value $VE_{REPOS}$ can result, therefore, in an adjustment of the stimulation frequency that is not properly related to real needs of the wearer of the device.

OBJECTS AND SUMMARY OF THE INVENTION

It is, therefore, an object of the present invention to propose, in an active implantable medical device, notably a cardiac pacemaker enslaved to a parameter by the intermediary of at least one sensor, a process to supervise continuously the level of activity of this sensor so as to establish an appropriate rest value that will allow an improved and more correct calibration of the enslavement function.

Another object of the present invention is to propose a process for distinguishing between different phases of rest of the wearer of the device, for example, rest during sleep periods and rest during awake periods, as well as other phases of activity, for example, activity during sleep and activity during awake periods and changing the operation of the device according to the detected phase.

Up until now, such a distinction in phases has been made in an arbitrary and approximate manner, based on an internal clock triggering at a fixed time some adjustments of the device. See, e.g., U.S. Pat. No. 5,143,065.

Broadly, the present invention provides an improvement on the known techniques by allowing one to determine a criterion, hereinafter referred to as the "activity criterion of the sensor" (also called the "activity criterion"), which corresponds well to the different phases of rest and activity of the wearer of the device.

To this end, one aspect of the invention is directed to a process of determining a criterion of activity of a sensor by measuring a parameter which serves to control at least one function in an active implantable medical device. One such method is characterized by the following steps:

a) acquiring successive samples of a value representative of the parameter from a signal collected by the sensor;

b) calculating over a first interval of time a first average value of the activity of the sensor from the acquired samples;

c) calculating over a second interval of time a second average value of the activity of the sensor from the acquired samples, the second interval being greater than the first interval; and d) determining the criterion of activity of the sensor based on a comparison of the first average value and the second average value.

The first and/or the second time intervals can be defined by either an internal clock of the device or a count of a preselected number of samples acquired by the sensor, notably a number of samples selected from between 1 and 1024, and preferably 128, samples.

The present invention also includes a certain number of advantageous subsidiary characteristics, as follows. The second time interval preferably has a duration on the order of 24 hours. Preferably, the end of a 24 hour period starts a new cycle such that second average value is recalculated every 24 hours. Alternatively, the second average value may be a sliding average corresponding to the samples acquired over the last 24 hours.

Preferably, the criterion of activity of the sensor is a binary criterion. Hence, at the method step d above, the criterion of activity is thus set to a first value, defining a state of rest of the patient, if the first average value is less than the second average value, and is otherwise set to a second value, defined as a non-rest state.

It also is anticipated that another determining step, based on the second average value calculated at step c), and two limits (a maximum limit and a minimum limit), may be implemented to determine a value of minimal activity of the sensor. This value is useful for controlling the function of the active implantable medical device. The value of minimal activity level of the sensor can be, in particular, a value that ranges between the maximum limit and the minimum limit. The minimum limit is preferably determined by the application of a predetermined coefficient to the second average value, preferably an integer multiple. The maximum limit is preferably determined by the application of another predetermined coefficient to the second average value, preferably in this case a coefficient of 1.5.

In a preferred embodiment, the aforementioned function controlled by the criterion of activity of the sensor is a function of enslavement of the active medical device. The determined value of the minimal activity level of the sensor can very advantageously be a value of adjustment from the low point of the calibration of the enslavement function of the active medical device. The calibration refers to the relation between the sensed parameter and the operating state of the device at that sensed parameter.

BRIEF DESCRIPTION OF THE DRAWINGS

Other characteristics and advantages of the invention will become apparent in the description below of a preferred embodiment of the invention, which is made with reference to the drawings annexed, in which like reference numerals refer to like elements, and in which.

DETAILED DESCRIPTION OF THE INVENTION

For clarity of the description, the following discussion makes reference to a sensor of a physiological parameter that is the "minute-ventilation". But the invention is equally applicable to the use of other physiological parameters, such as those parameters indicated in the introduction of the present description. The invention is also applicable to any physiological parameter that can be sensed or measured, and then used for functions such as an enslavement of active implantable device (and for functions other than enslavement), which can be substituted for the minute—ventilation, without departing from the scope and framework of the present invention. In addition, the principles of the present invention can be extended to the enslavement of an active implantable device by a non-physiological parameter such as the acceleration (patient exercise or motion) measured by a sensor, typically a sensor, such as an accelerometer, internal to the device case. Such devices are described, for example, in the U.S. Pat. No. 5,330,510.

The measure of the minute-ventilation is in itself well known. It is described in, for example, the document "Breath-by-Breath Minute Ventilation Measurement Can Provide A Fast Response", by J. L. Bonnet, L. Kramer, Mr. Limousin, EUR. J.C.P.E., 1994, Vol. 4, Abstract Number 329. It also is commercially realized in the device sold under the trade name and model CHORUS RM 7034, manufactured by the ELA Medical, Montrouge, France.

Furthermore, the process described herein is preferably implemented using a hardware architecture that includes a microprocessor executing programming instructions from a ROM memory, and having analog and digital logic circuits in themselves known. Such a microprocessor-based structure is, for example, employed in the CHORUS model series of cardiac pacemakers manufactured by ELA Medical. More particularly, the present invention has been implemented in a rate responsive pacemaker under the trade name CORUM 7234 available from ELA Medical, and uses such a microprocessor based architecture. Alternatively, the process may be implemented in an architecture having hardwired discrete and dedicated logic circuits. Although it does not have all of the advantages, including the flexibility, of a realization of the invention in a microprocessor based device, a hardwired structure is nevertheless perfectly foreseeable to be used for the invention, and is equally within the scope and framework of the present invention.

Set forth in the following discussion is a description of the various modes of a preferred embodiment of the process of the invention, which may be implemented in a suitable hardware architecture.

Figure 1:
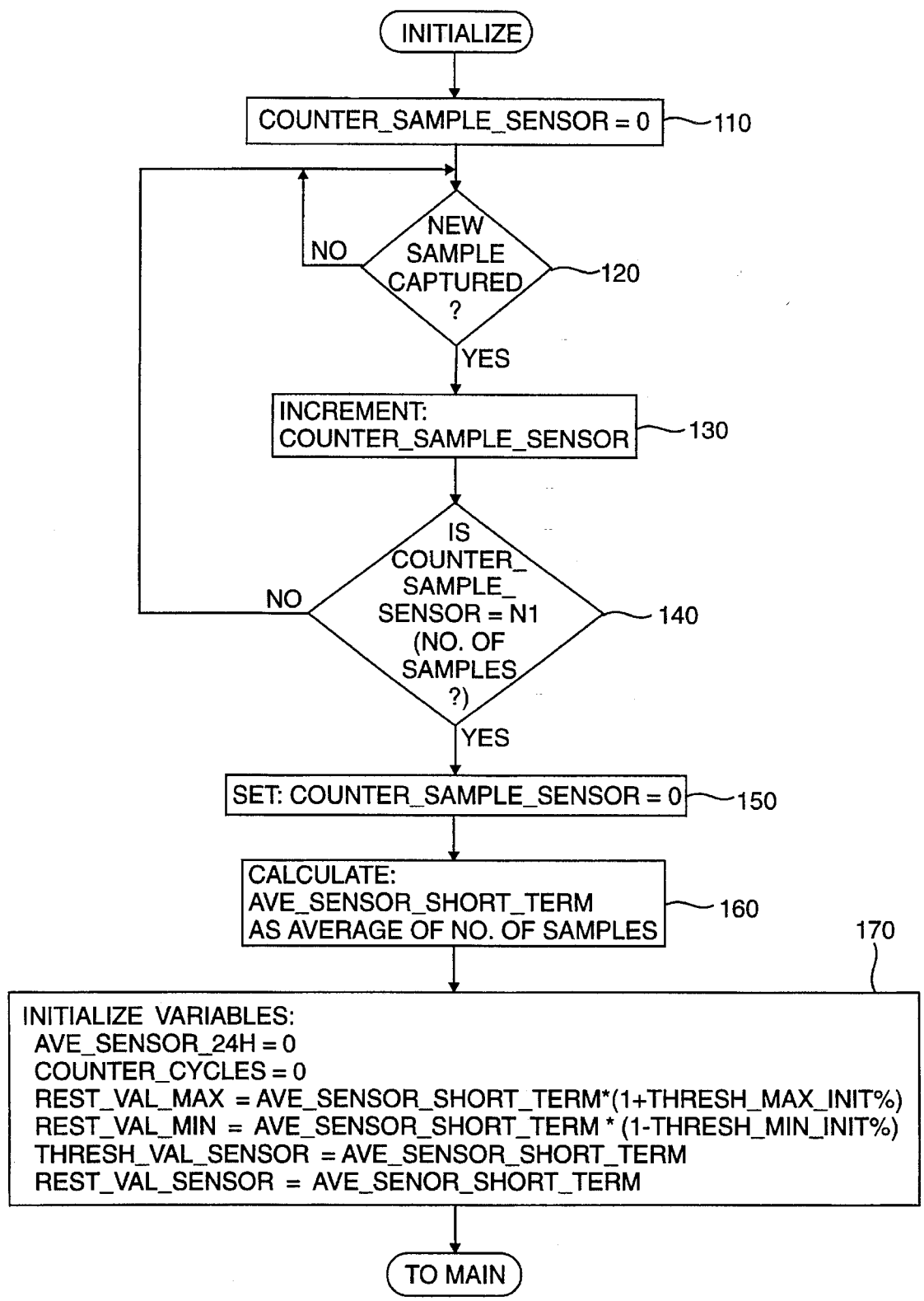
FIG. 1 is a flow chart of the initialization phase of a process in accordance with an embodiment of the invention, which may be in response to an initial operation (start-up) or a manual re-initialization as may be initiated by a therapist.

With reference to FIG. 1, the process of the phase of initialization is illustrated. The initialization phase process broadly concerns the calculation of several variables. It is noted that the calculation of certain variables (e.g., AVE_SENSOR_24H, THRESH_VAL_SENSOR and REST_VAL_SENSOR, that will be explained in more detail below), can be undertaken according to at least two different modes, depending on whether or not the device is in an initialization phase or in the regime of normal continuous functioning, which regime is referred to as "normal functioning phase".

The phase of initialization is brought out, i.e., used, when the medical device is first placed into operation, for example, at the time of implantation, or on a specific external command (i.e., a reset function, as may be delivered telemetrically in a known manner). The initialization phase has as its purpose and objective to endow the device with an initial value that will then be automatically and subsequently redetermined over time in the normal functioning phase.

In the initialization phase, the device acquires and stores in memory a predetermined number of minute ventilation values, corresponding, typically, to 32 samples of the measure of the minute—ventilation (steps 110 to 140). Each sample corresponds to the determination of the minute—ventilation (MV) during a respiratory cycle. A counter referred to as COUNTER_SAMPLE_SENSOR is used to control the acquisition of the sample measures. The counter COUNTER_SAMPLE_SENSOR is reset to zero (step 100) at the start of the initialization phase, and increments (step 130) one count after each sample is successively acquired (step 120).

When the value of the counter COUNTER_SAMPLE_SENSOR reaches the predetermined number N1, e.g., N1=32, the counter is reset to zero (step 150) and the device then calculates an average of the 32 successively acquired values. This average is referred to as AVE_SENSOR_HORT_TERM (step 160).

At step 170, the different variables used in the process of invention are then initialized. The counter COUNTER_CYCLES_24H and the variable AVE_SENSOR_24H are reset to 0, the variables THRESH_VAL_SENSOR and REST_VAL_SENSOR are set to the value $AVE_{\_SENSOR\_}$ SHORT_TERM that was determined at step 160. The variable REST_VAL_MAX is set to a value that is related to the determined AVE_SENSOR_SHORT_TERM by a first predetermined coefficient (1+THRESH_MAX_INIT%), typically increased by 50%, and the variable REST_VAL_MIN is set to a value that is related to the determined AVE_SENSOR_SHORT_TERM by a second predetermined coefficient (1−THRESH_MIN_INIT%), typically decreased by 50%.

These initialized variables then serve as the initial values in the normal functioning phase, which is now described with reference to FIGS. 2 to 8.

Figure 2:
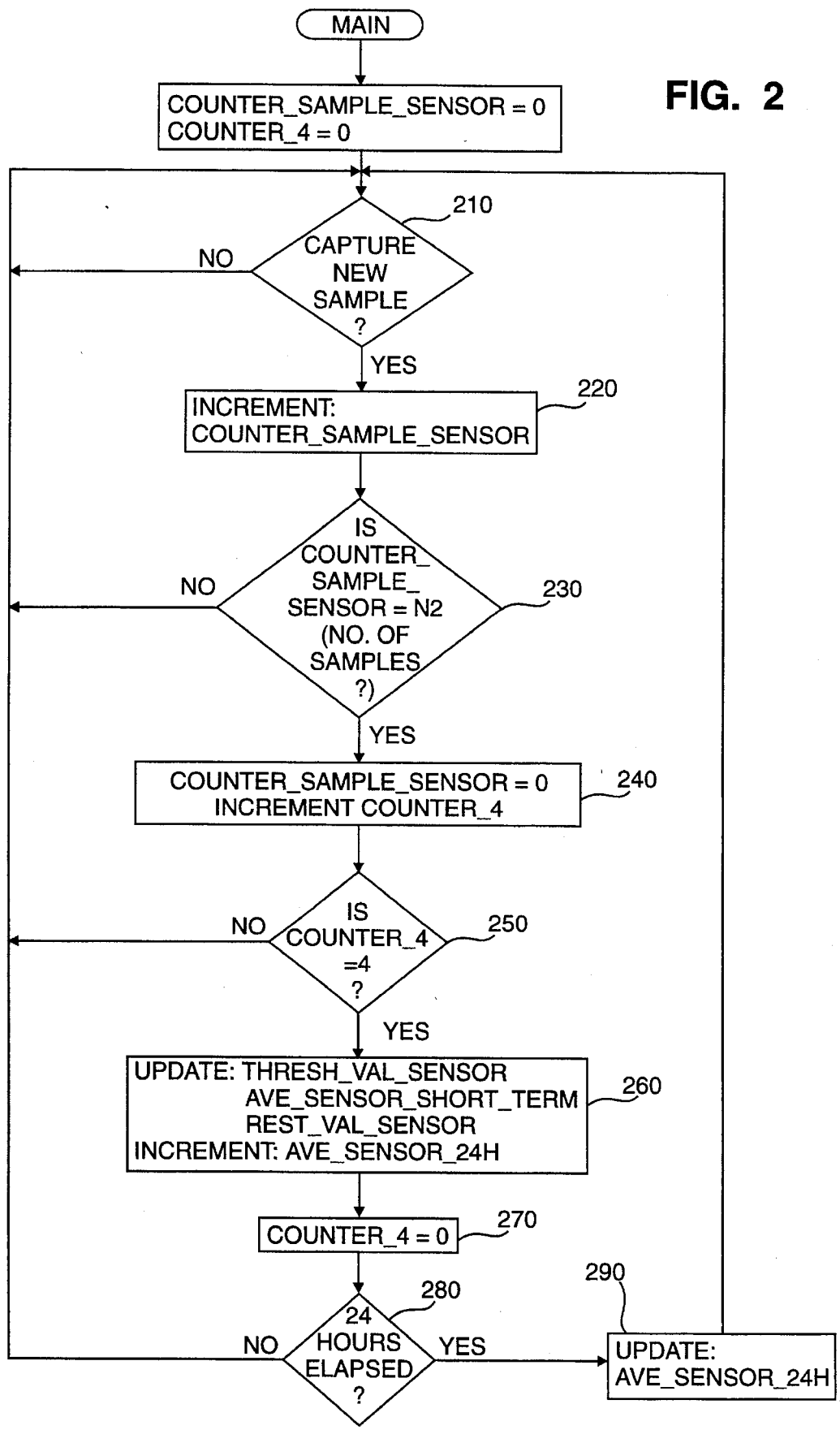
FIG. 2 is a flow chart of a normal functioning phase, during the course of which one continuously determines different variables according to the invention.

The general progress of the normal functioning phase is illustrated in a general manner in FIG. 2. The implantable device executes the following steps: At step 200, the two counters COUNTER_SAMPLE_SENSOR and COUNTER_4 are reset to zero, and in steps 210 to 250 a selected number N2 of successive samples as obtained by the sensor are collected and stored in a memory.

After 128 samples have been collected, that is to say after four repetitions of the collection of 32 samples, namely when COUNTER_SAMPLE_SENSOR=N2=32 and COUNTER_4=4 at step 250, the device then updates the variables at step 260. The variable THRESH_VAL_SENSOR is updated, in accordance with the process illustrated in the flow chart of FIG. 3. The variable AVE_SENSOR_SHORT_TERM is calculated as an average of the 128 previously measured samples (it being understood that the, numbers of 128; 32 samples and 4 cycles, are exemplary and not limiting, and each can be replaced by a different value, as appropriate for the memory of the device and its processing power). The REST_VAL_SENSOR is updated in accordance with the process illustrated in the flow chart of FIG. 4; and the variable AVE_SENSOR_24H is updated in accordance with the process illustrated in the flow chart of FIG. 5.

Figure 3:
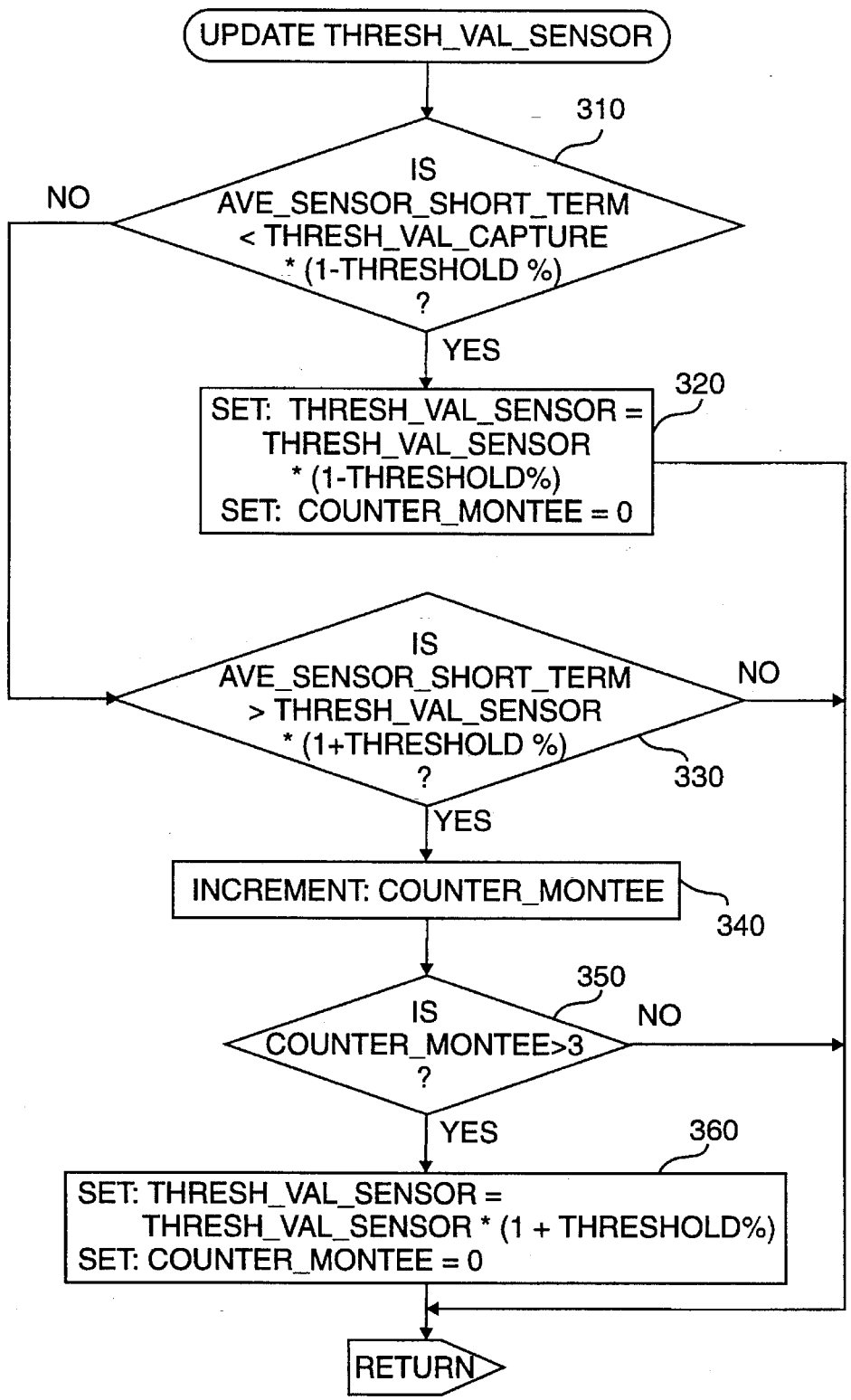
FIG. 3 is a flow chart of a process to update the variable THRESH_VAL_SENSOR of the process illustrated in FIG. 1.

Referring to FIG. 3, the periodic update of the variable THRESH_VAL_SENSOR in a preferred embodiment is described. First, this variable serves to determine the level of activity of the sensor at the end of step 260, that is to say after 128 cycles of sample measurement. It is used in addition for the calculation of variables REST_VAL_SENSOR and AVE_SENSOR_24H. It is calculated of the following manner. If the value of AVE_SENSOR_SHORT_TERM is comprised within the limits bounded by THRESH_VAL_SENSOR±THRESHOLD% (where the THRESHOLD% is a predetermined value, typically 6.25%), then THRESH_VAL_SENSOR is not modified (steps 310 and 330). If, however, the value of AVE_SENSOR_SHORT_TERM has become less than THRESH_VAL_SENSOR_THRESHOLD%, one considers that the acquired (sensed) activity level has decreased, and one decreases then the variable THRESH_VAL_SENSOR by a quantity THRESHOLD%, and resets to zero the counter COUNTER_MONTEE (steps 310 and 320), and if the value of AVE_SENSOR_SHORT_TEPM has become greater than THRESH_VAL_SENSOR+THRESHOLD%, then one increases the counter COUNTER_MONTEE by one count (steps 310, 330 and 340).

If the counter COUNTER_MONTEE reaches a predetermined count value, e.g., 4 (a number chosen in an arbitrary manner, but corresponding to a typical situation), one considers that the sensed activity level has increased, and one increases then THRESH_VAL_SENSOR by a quantity THRESHOLD%, and resets to zero COUNTER_MONTEE (steps 350 and 360).

Figure 4:
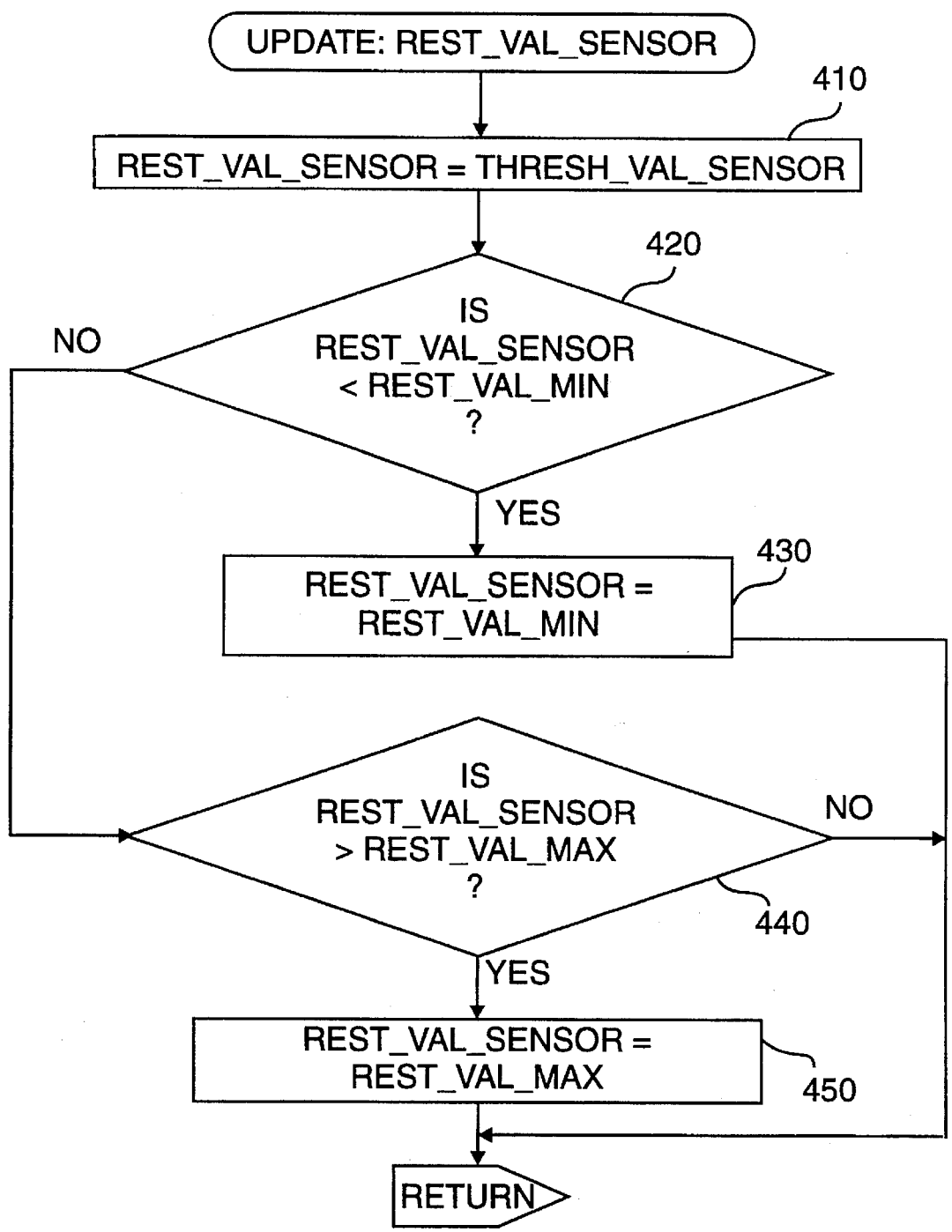
FIG. 4 is a flow chart of a process to update the variable REST_VAL_SENSOR of the process illustrated in FIG. 1.

Referring to FIG. 4, the periodic update of the variable REST_VAL_SENSOR is described. The value REST_VAL_SENSOR has a default value which is the previously determined THRESH_VAL_SENSOR at step 410.

But REST_VAL_SENSOR is nevertheless limited to two limits depending on AVE_SENSOR_24H, such that: If REST_VAL_SENSOR is less than REST_VAL_MIN, then the value of REST_VAL_SENSOR is set equal to the value of REST_VAL_MIN (steps 420 and 430); If REST_VAL_SENSOR is greater than REST_VAL_MAX, then the value of REST_VAL_SENSOR is set equal to the value REST_VAL_MAX (steps 420, 440 and 450). The determination of the values REST_VAL_MIN and REST_VAL_MAX are explained hereafter, with reference to FIG. 6, especially in the case where these values do not correspond to those established during the initialization phase (step 170).

Figure 5:
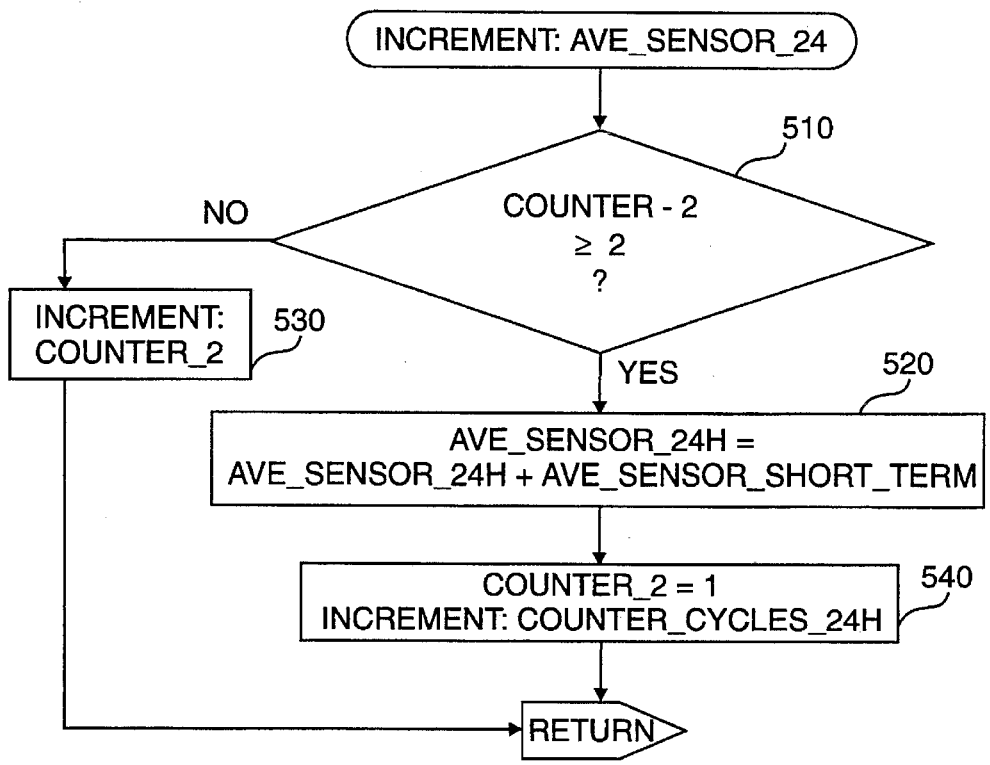
FIG. 5 is a flow chart of a process to increment the variable AVE_SENSOR_24H of the process illustrated in FIG. 1.
Figure 6:
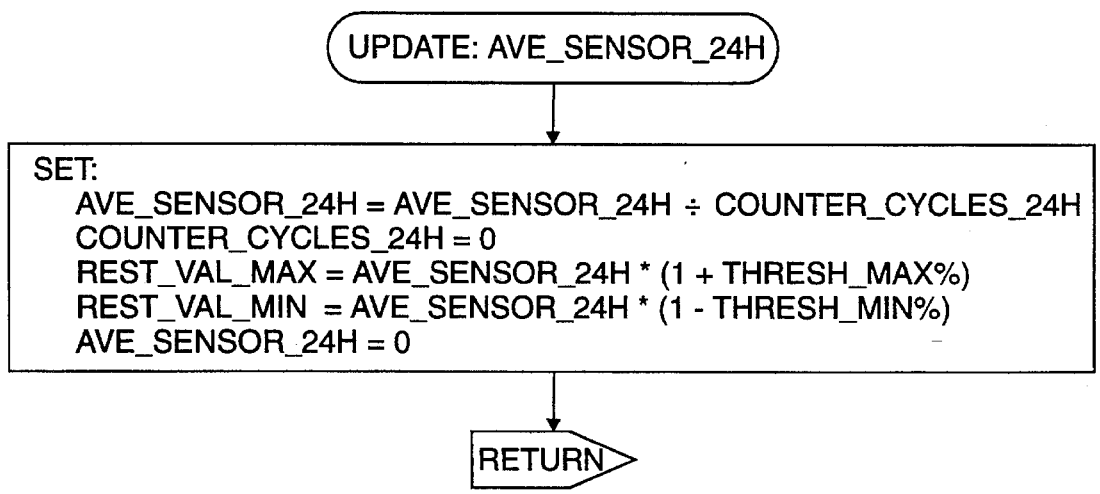
FIG. 6 is a flow chart of a process to update the variable AVE_SENSOR_24H of the process illustrated in FIG. 1.

Referring to FIGS. 5 and 6, the determination of the variable AVE_SENSOR_24H is described. This variable is first incremented in manner specified on the flow chart of FIG. 5, which is implemented during the course of step 260 of the process shown in FIG. 2. Following the value of COUNTER_2 (a counter that can have only two values, e.g., 1 or 2), one increases the variable AVE_SENSOR_24H by the value of AVE_SENSOR_SHORT_TERM at step 520, and one increments a counter COUNTER_CYCLES_24H at step 540.

At the end of a period of 24 hours (step 280 of FIG. 2), which is calculated from either an internal clock signal of the device or from a number of iterations of preceding phases corresponding approximately to a duration of 24 hours, the device updates the variable AVE_SENSOR_24H (step 290 of FIG. 2).

The different operations resulting in this update of AVE_SENSOR_24H are clarified in step 610 of FIG. 6. More precisely, the variable AVE_SENSOR_24H takes the value of the average of the sum of AVE_SENSOR_24H established at step 520, an average that is calculated by dividing the total of the sum by the value COUNTER_CYCLES_24H determined at step 540, as described above (FIG. 5).

At step 610 (FIG. 6), the device then sets the values REST_VAL_MAX and REST_VAL_MIN, calculated from preceding result by the value AVE_SENSOR_24H. The maximal value, REST_VAL_MAX, of the REST_VALUE range, is set equal to AVE_SENSOR_24H×(1+ THRESH_MAX%), typically THRESH_MAX is a predetermined value, e.g. 50%. The minimal value, REST_VAL_MIN, of the REST_VALUE range is set equal to AVE_SENSOR_24H×(1−THRESH_MIN%). Typically THRESH_MIN% is a predetermined value and may be, e.g. 0.

At the end of the step 610, AVE_SENSOR_24H and COUNTER_CYCLES_24H are initialized to zero.

One will note that the determination of the variable REST_VALUE, in combination with the two extreme variation boundary limits REST_VAL_MAX and REST_VAL_MIN (themselves dependent on the variable AVE_SENSOR_24H) allows to establish, in a manner perfectly appropriate, the low point of the automatic calibration curve of the enslavement function that is described in the aforementioned EP-A-0 493 222, which is incorporated herein by reference, where one will be able to make correspond to define a relationship between REST_VALUE and the frequency of stimulation $Fc_{base}$ programmed by the therapist.

Figure 7:
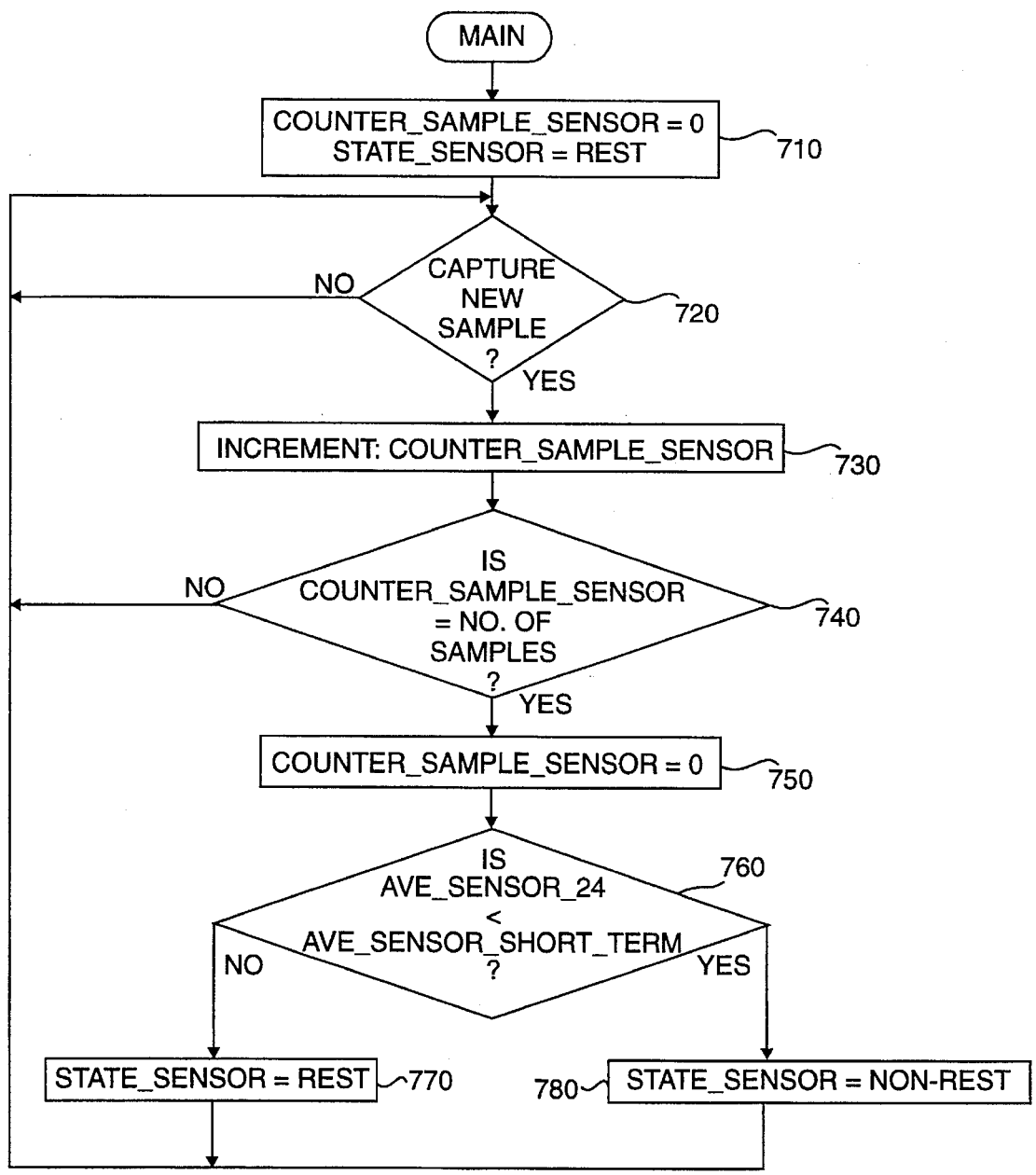
FIG. 7 is a flow chart of a process to determine the variable STATE_SENSOR in the case of the utilization of a physiological parameter (ventilation—minute, temperature, etc.)
Figure 8:
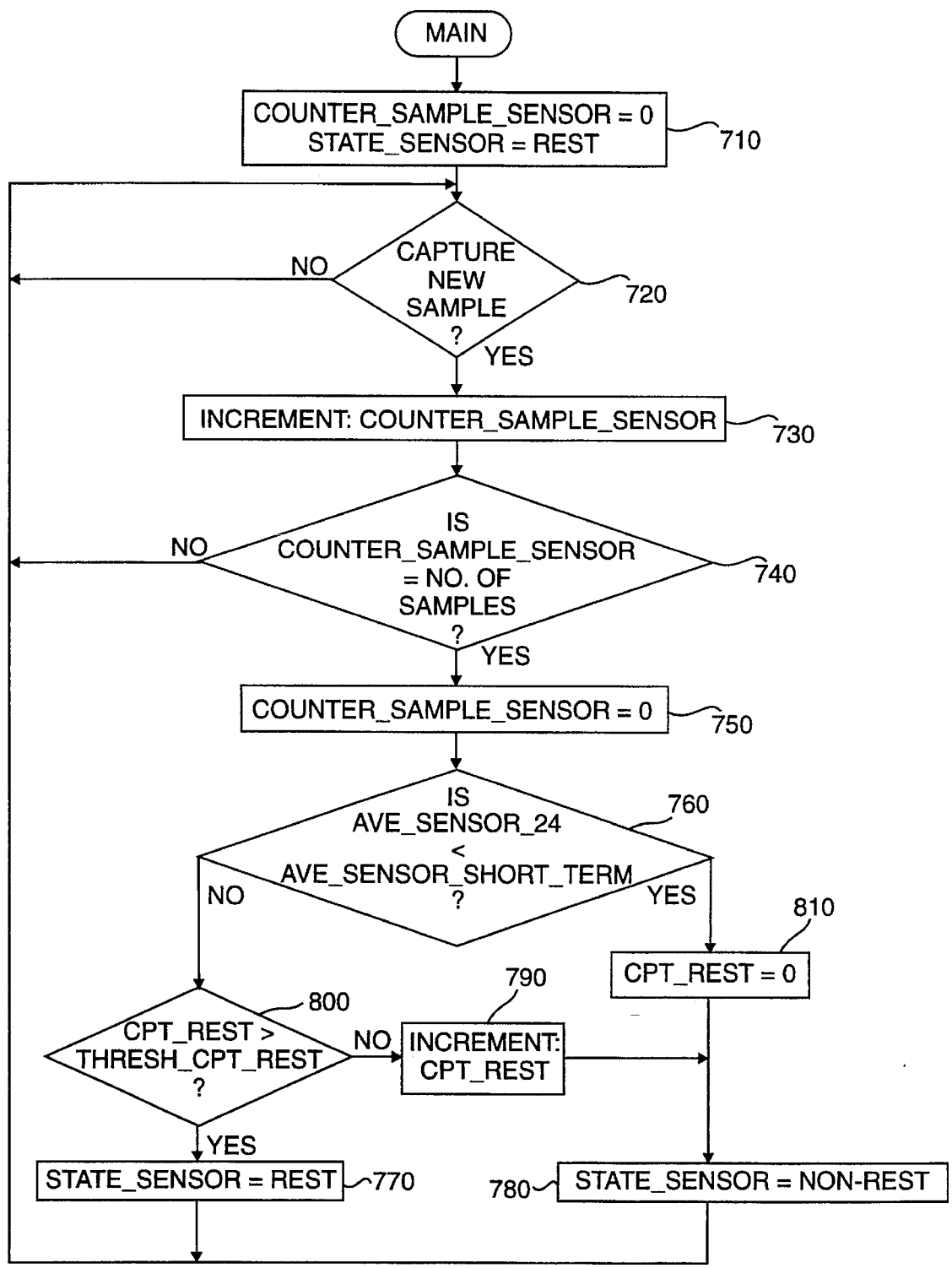
FIG. 8 is a flow chart of a process to determine the variable STATE_SENSOR in the case of the utilization of a non-physiological parameter such as acceleration.

The "criterion of sensor activity" defined above, corresponding in a variable STATE_SENSOR, is determined in accordance with the flow chart illustrated in FIGS. 7 or 8, depending on the type of enslavement sensor used.

After a phase of initialization (step 710) and after a number of cycles corresponding to the value of COUNTER_SAMPLE_SENSOR, that is, typically after 32 cycles (steps 720 to 750), the device compares the variable AVE_SENSOR_24H and AVE_SENSOR_SHORT_TERM (step 760). If AVE_SENSOR_SHORT_TERM is less than AVE_SENSOR_24H, the device considers that the average level of activity for that period is below the average level of activity over a period 24 hours, and, therefore, the patient is reliably determined to be in a proven rest state (for example, a nocturnal sleep phase). The device then sets the value of STATE_SENSOR to "Rest" (step 770). In the opposite case, it considers that there is no rest, that the patient is alert and active, and sets the value of STATE_SENSOR to "Non-Rest" (step 780).

For a non-physiological sensor (for example, a sensor of acceleration), the flow chart of the FIG. 7 is slightly modified, as in the manner illustrated in FIG. 8. In this case, a counter CPT_REST is employed; it is reset to zero at the initial step 710 and incremented (step 790) each time that the device determines that the patient is in a proven state of rest. If this situation repeats a predetermined number of times, designated THRESH_CPT_REST, typically on the order 12 repetitions during the 24 hour period (step 800), then the value of STATE_SENSOR is set to "Rest" (step 770). In the opposite case, one re-initializes CPT_REST to 0 (step 810) and sets STATE_SENSOR to "Non-Rest" (step 780). One will note incidentally that the flow chart of FIG. 7 corresponds in fact to a simplified version of that of FIG. 8, with THRESH_CPT_REST=0.

In an alternative embodiment, one can replace the counter incrementation and the test of the number of occurrences of samples acquired, by a test conducted over a fixed period defined by the internal clock of the device, for example, a fixed period of 10 minutes can be used to acquire the data used to calculate the short term average.

Figure 9:
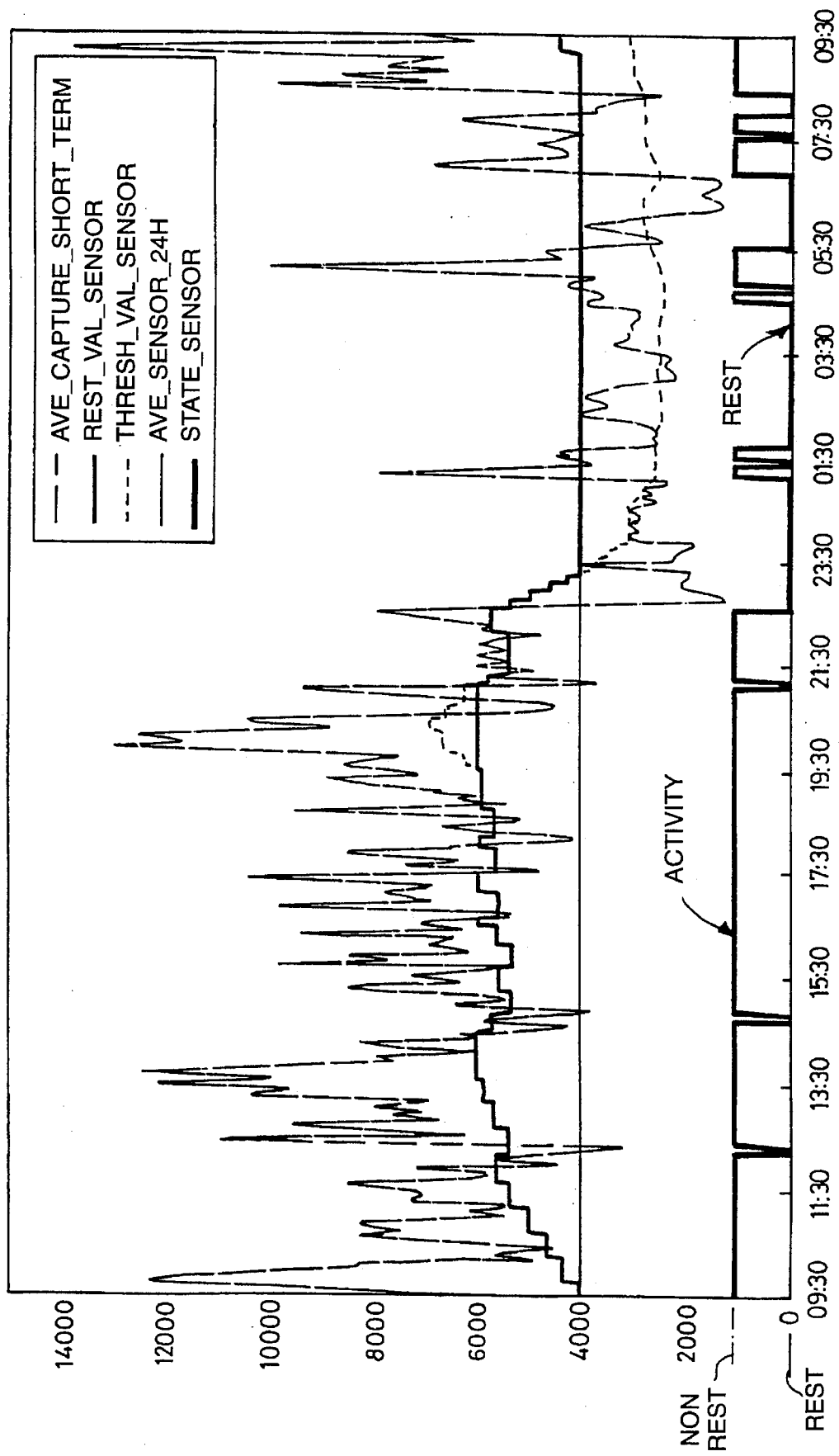
FIG. 9 is an illustration showing the evolution over time of the different variables of the process of the invention, recorded during an exemplary 24 hour time interval.

FIG. 9 illustrates an example of the evolution of the different variables THRESH_VAL_SENSOR, AVE_SENSOR_SHORT_TERM, REST_VAL_SENSOR and AVE_SENSOR_24H, over a 24 hour period as well as of the activity criterion STATE_SENSOR determined accordingly to the process of the invention. One can note that, during the phase of sleep between 23:00 hours (11:00 pm) and 6:00 hours (6:00 am), the variable STATE_SENSOR is preponderantly set to the state "Rest", and includes Non-Rest states.

The information given by the variable STATE_SENSOR thus will be able to be used by the device to trigger various functions necessitating or exploiting the knowledge of the Rest phases of the wearer of the device. It will be appreciated that by the use of additional thresholds, averages, and coefficients, multiple states of relative rest and activity may be defined for use by the device.

One skilled in the art will appreciate that the present invention can be practiced by other than the described embodiments, which are presented for purposes of illustration and not of limitation.

I claim:

1. A process for determining a criterion of activity of a sensor for measuring a parameter serving to control at least one function in an active implantable medical device, comprising the steps of:

a) acquiring successive samples of a representative value of the parameter from a signal collected by the sensor;

b) calculating over a first interval of time a first average value (AVE_SENSOR_SHORT_TERM) of the activity of the sensor from the samples acquired during said first time interval;

c) calculating over a second interval of time, the second time interval being greater than the first, a second average value (AVE_SENSOR_24H) of the activity of the sensor from the samples acquired during said second time interval; and d) determining a criterion of activity of the sensor based on a comparison of the first average value and the second average value.

2. The process of claim 1, further comprising the step of defining at least one of the first and the second time intervals using an internal clock of the device.

3. The process of claim 1, further comprising the step of defining at least one of the first and second time intervals by counting a number of samples acquired by the sensor.

4. The process of claim 3, further comprising defining the first time interval by counting a number of samples selected from between 1 and 1024 samples.

5. The process of claim 1, further comprising providing the second time interval as a duration of approximately 24 hours.

6. The process of claim 1, further comprising providing the criterion of activity of the sensor as a binary criterion having a first state and a second state (Rest, Non-Rest).

7. The process of claim 6, wherein step d) further comprises setting the criterion of activity to a first value (Rest) defining a state of rest of the patient in response to the first average value (AVE_SENSOR_SHORT_TERM) being less than the second average value (AVE_SENSOR_24H), and a second value (Non-Rest) defining a state of non-rest of the patient in response to the second average value being less than the first average value.

8. The process of claim 1, further comprising a step of determining a first value of minimal activity level and a second value of maximal activity level of the sensor as respective functions of the second average value (AVE_SENSOR_24H) calculated at step c).

9. The process of claim 8, wherein determining the first value of minimal activity level of the sensor further comprises limiting an excursion of the first value to a range between an upper limit and a lower limit.

10. The process of claim 9, further comprising providing the lower limit by applying a predetermined coefficient (1−THRESH_MIN%) to the second average value.

11. The process of claim 10 wherein providing the lower limit further comprises providing an integer coefficient.

12. The process of claim 9, further comprising providing the upper limit by applying a predetermined coefficient (1+THRESH_MAX%) to the second average value.

13. The process of claim 12 wherein providing the upper limit further comprises providing a coefficient of approximately 1.5.

14. The process of claim 1, further comprising controlling a function of enslavement of the active implantable medical device by the criterion of activity of the sensor.

15. The process of claim 1, further comprising steps of:
    i) providing a lower limit by applying a predetermined coefficient (1−THRESH_MIN%) to the second average value;
    ii) providing an upper limit by applying a predetermined coefficient (1+THRESH_MAX%) to the second average value;
    iii) determining a value of minimal activity level of the sensor (REST_VAL_SENSOR) for the aforementioned control function of the active implantable medical device as a function of the second average value (AVE_SENSOR_24H) calculated as step c), and the upper limit and the lower limit; and
    iv) limiting an excursion of the value to a range between the upper and lower limits.

16. The process of claim 15 further comprising controlling a function of enslavement of the active implantable medical device by the criterion of activity of the sensor, and providing a value of adjustment of the low point of the calibration of the function of enslavement of the active implantable medical device as the value of the minimal activity level of the sensor (REST_VAL_SENSOR).

17. Apparatus for determining a criterion of activity of a sensor for measuring a parameter serving to control at least one function in an active implantable medical device, comprising:
    a sensor for measuring a device function control parameter;
    means, responsive to the sensor, for acquiring successive samples of a representative value of the measured parameter;
    first means for calculating a first average value of the activity of the sensor from the samples acquired during a first time interval;
    second means for calculating a second average value of the activity of the sensor from the samples acquired during a second time interval, the second time interval being greater than the first; and
    means for determining a criterion of activity of the sensor based on a comparison of the first average value and the second average value.

18. The apparatus of claim 17 further comprising an internal clock wherein at least one of the first and the second time intervals is based on the internal clock.

19. The apparatus of claim 17, further comprising a counter having a count corresponding to a number of acquired samples wherein at least one of the first and second time intervals is defined by the counter count reaching a preselected value.

20. The apparatus of claim 19 wherein the first time interval is defined by the counter count reaching a number of samples selected from between 1 and 1024 samples, and wherein the second time interval is a duration of approximately 24 hours.

21. The apparatus of claim 17, wherein the criterion of activity of the sensor is a binary criterion having a first state and a second state.

22. The apparatus of claim 17, wherein the determining means further comprises means for comparing the first average value and the second average value, and the criterion of activity is set to a first value defining a state of rest of the patient in response to the first average value being less than the second average, and a second value defining a state of non-rest of the patient in response to the first average value not being less than the second average value.

23. The apparatus of claim 22 wherein the aforementioned function controlled by the criterion of activity of the sensor is a function of enslavement of the active implantable medical device and the value of the minimal activity level of the sensor further comprises a value of the adjustment of the low point of the calibration of the function of enslavement of the active implantable medical device.

24. The apparatus of claim 17, further comprising means for determining a value of minimal activity level of the sensor for the aforementioned control function of the active implantable medical device as a function of the second average value, wherein the second average value is limited to a value in a range between an upper limit and a lower limit.

25. The apparatus of claim 24, wherein the lower limit is a function of a first predetermined coefficient applied to the second average value, and the upper limit is a function of a second predetermined coefficient applied to the second average value.

26. The apparatus of claim 25 wherein the first predetermined lower limit is an integer coefficient and the second predetermined coefficient is approximately 1.5.

27. The apparatus of claim 17 wherein the aforementioned function controlled by the criterion of activity of the sensor is a function of enslavement of the active implantable medical device.

* * * * *